(12) United States Patent
Rabbani

(10) Patent No.: US 11,723,895 B2
(45) Date of Patent: Aug. 15, 2023

(54) SPHINGOSINE PATHWAY MODULATING COMPOUNDS FOR THE TREATMENT OF CORONAVIRUS INFECTION

(71) Applicant: Enzo Biochem, Inc., New York, NY (US)

(72) Inventor: Elazar Rabbani, New York, NY (US)

(73) Assignee: ENZO BIOCHEM, INC., Farmingdale, NY (US)

( * ) Notice: Subject to any disclaimer, the term of this patent is extended or adjusted under 35 U.S.C. 154(b) by 6 days.

(21) Appl. No.: 17/197,100

(22) Filed: Mar. 10, 2021

(65) Prior Publication Data

US 2021/0290567 A1 Sep. 23, 2021

Related U.S. Application Data

(60) Provisional application No. 62/990,638, filed on Mar. 17, 2020.

(51) Int. Cl.
*A61K 31/137* (2006.01)
*A61K 31/4245* (2006.01)

(52) U.S. Cl.
CPC ........ *A61K 31/4245* (2013.01); *A61K 31/137* (2013.01)

(58) Field of Classification Search
None
See application file for complete search history.

(56) References Cited

U.S. PATENT DOCUMENTS

| | | |
|---|---|---|
| 8,314,151 B2 | 11/2012 | Spiegel et al. |
| 8,372,888 B2 | 2/2013 | Zipkin et al. |
| 2003/0059447 A1 | 3/2003 | Lambers |
| 2007/0185027 A1 | 8/2007 | Erickson et al. |
| 2011/0172202 A1 | 7/2011 | Martinborough et al. |
| 2013/0231326 A1 | 9/2013 | Martinborough et al. |
| 2015/0299149 A1 | 10/2015 | Martinborough et al. |
| 2018/0235907 A1 | 8/2018 | Spiegel et al. |
| 2018/0369169 A1 | 12/2018 | Rabbani et al. |
| 2020/0113850 A1* | 4/2020 | Gulbins ................. A61P 31/16 |

OTHER PUBLICATIONS

Zhu et al. (N Engl J Med 382 (8): 727-733, Feb. 20, 2020).*
Bakowski et al., "Oral drug respoitioning candidates and synergistic remdsivir combinations for the prophylaxis and treatment of COVID-19," *bioRxivl*, https://dol.org/10.1101/2020.06.16.153403, 17 pages (2020).
Berger et al., "COVID-19 and MS disease-modifying therapies," *Neurol Neuroimunnol Neuroinflamm*, vol. 7, e761, 9 pages (2020).
COVID-19 Ozanimod Intervention Study, ClinicalTrials.gov, 8 pages (2021).
McGowan et al., "Targeting the SphK-S1P-SIPR Pathway as a Potential Therapeutic Approach for COVID-19," *Molecular Sciences*, vol. 21, 36 pages (2020).
Naz et al., "Battling COVID-19 Pandemic Sphingosine-1-Phosphate Analogs as an Adjunctive Therapy?, " *Frontiers in Immunology*, vol. 11, Article, 1102, 4 pages (2020).
Paugh et al., "A selective sphingosine kinase 1 inhibitor integrates multiple molecular therapeutic targets in human leukemia," *Blood*, vol. 112, No. 4, pp. 13821391 (2008).
Scott et al., "Organized (RPC1063) is a potent sphingosine-1-phosphate receptor-1 (S1P[1]) and receptor-5 (S1P[5]) agonist with autoimmune disease-modifying activity," *The British Pharmacological Society*, vol. 173, pp. 1778-1792 (2016).

* cited by examiner

*Primary Examiner* — Bong-Sook Baek
(74) *Attorney, Agent, or Firm* — Quarles & Brady LLP

(57) ABSTRACT

The invention provides methods and compositions for treating a coronavirus infection using sphingosine kinase-1 inhibitors, such as SK1-I, and selective sphingosine-1-phosphate receptor agonists, such as ozanimod.

6 Claims, No Drawings

SPHINGOSINE PATHWAY MODULATING COMPOUNDS FOR THE TREATMENT OF CORONAVIRUS INFECTION

CROSS-REFERENCE TO RELATED APPLICATIONS

This application claims the benefit of U.S. provisional application Ser. No. 62/990,638 filed Mar. 17, 2020, which is hereby incorporated by reference in its entirety.

FIELD OF THE INVENTION

The invention relates to the field of pharmaceutical treatment of viral infections.

BACKGROUND

Sphingosine-1-phosphate (S1P) was discovered to be a bioactive signaling molecule over 20 years ago. Studies have since identified two related kinases, sphingosine kinase 1 and 2 (a/k/a sphingosine kinase "type I" and "type II" respectively, and SphK1 and SphK2 respectively), which catalyze the phosphorylation of sphingosine to S1P. Extracellular S1P can bind to and activate each of five S1P-specific, G protein-coupled receptors (designated $S1PR_{1-5}$) to regulate cellular and physiological processes in an autocrine or paracrine manner. Selective inhibitors of each of sphingosine kinase 1 and 2, as well as both non-selective and selective agonists of S1PRs, have been developed and are known in the art.

SUMMARY

One embodiment of the invention provides a method for treating coronavirus infection in a mammalian subject, such as a human, that includes the step of:

administering to a mammalian subject in need of treatment for a coronavirus infection, such as severe acute respiratory syndrome coronavirus 2 (SARS-CoV-2) infection, a therapeutically effective amount of a sphingosine kinase type I inhibitor or a pharmaceutically acceptable salt thereof, such as a sphingosine kinase type I inhibitor disclosed in U.S. Pat. Nos. 8,372,888 and/or 8,314,151, such as SK1-I, or a pharmaceutically acceptable salt thereof, for example a hydrochloride salt thereof.

A related embodiment of the invention provides a pharmaceutical composition that includes a sphingosine kinase type I inhibitor or a pharmaceutically acceptable salt thereof, such as SK1-I or a pharmaceutically acceptable salt thereof, for the treatment of coronavirus infection, such as severe acute respiratory syndrome coronavirus 2 (SARS-CoV-2), in a mammal, such as a human patient.

Another embodiment of the invention provides a method for treating a coronavirus infection in a mammalian subject, such as a human, that includes the step of:

administering to a mammalian subject in need of treatment for a coronavirus infection, such as severe acute respiratory syndrome coronavirus 2 (SARS-CoV-2) infection, a therapeutically effective amount of a sphingosine-1-phosphate receptor agonist, such as an agonist of one or both of sphingosine-1-phosphate receptor-1 ($S1P_1$) and sphingosine-1-phosphate receptor-5 ($S1P_5$) such as ozanimod (RPC1063) or a pharmaceutically acceptable salt thereof, or an active metabolite of ozanimod or a pharmaceutically acceptable salt thereof.

Additional features, advantages, and embodiments of the invention may be set forth or apparent from consideration of the following detailed description, drawings if any, and claims. Moreover, it is to be understood that both the foregoing summary of the invention and the following detailed description are exemplary and intended to provide further explanation without limiting the scope of the invention as claimed.

DETAILED DESCRIPTION

The invention provides new uses of sphingosine kinase-1 inhibitors, such as SK1-I, and selective sphingosine-1-phosphate receptor agonists, such as ozanimod, for treating coronavirus infections in mammalian subjects, such as human patients.

Sphingosine kinase 1 inhibitors used in various embodiments of the invention may, for example, include any of those disclosed in U.S. Pat. Nos. 8,372,888 and/or 8,314,151, each of which is hereby incorporated by reference in its entirety herein, or pharmaceutically acceptable salts thereof. The sphingosine kinase I inhibitor may, for example, be (E,2R,3S)-2-(methylamino)-5-(4-pentylphenyl)pent-4-ene-1,3-diol (also known as SK1-I), or a pharmaceutically acceptable salt thereof such as but not limited to a hydrochloride salt. The structure of SK1-I is shown below.

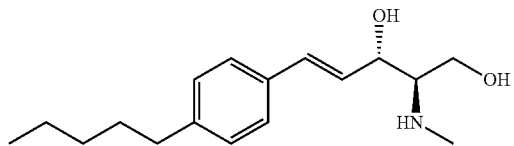 [SMILES: CCCCCc1ccc(/C=C/[C@H](O)[C@@H](CO)NC)cc1]

See also Paugh et al., Blood, 2008 112: 1382-1391.

The sphingosine kinase I inhibitor may, for example, be a compound having the structure

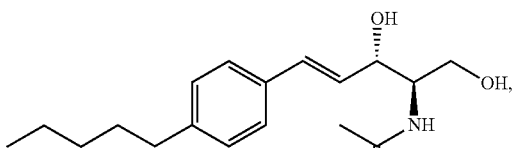

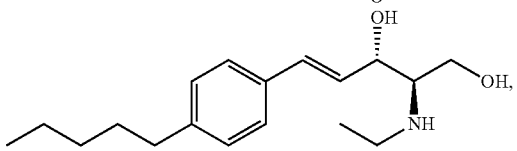

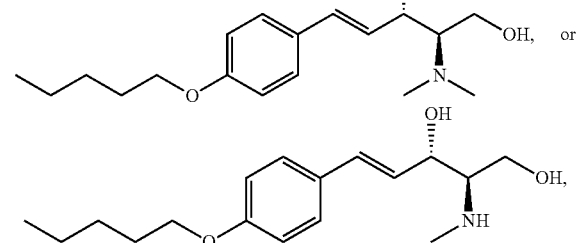

or a pharmaceutically acceptable salt of the compound such as but not limited to a hydrochloride salt.

The sphingosine kinase I inhibitor may, for example, be a compound having the structure

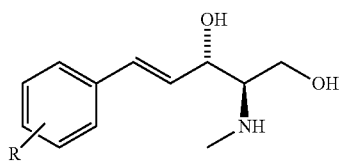

wherein R is selected from a straight carbon chain, a branched carbon chain, a straight carbon chain comprising one or more heteroatoms, a branched carbon chain comprising one or more heteroatoms, a cyclic ring, a heterocyclic ring, an aromatic ring, a hetero-aromatic ring, or any combination of the foregoing, or a pharmaceutically acceptable salt thereof such as but not limited to a hydrochloride salt.

The sphingosine kinase I inhibitor may, for example, be a compound having the structure

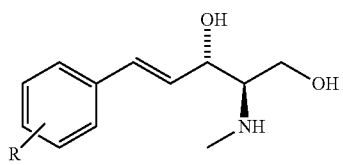

wherein R is 3,4-dimethoxy, 4-phenyl or 3-pentyl, or a pharmaceutically acceptable salt thereof such as but not limited to a hydrochloride salt.

Sphingosine-1-phosphate receptor agonists used in various embodiments of the invention may, for example, be any of those disclosed in any of U.S. Pub. Nos. 20110172202, 20130231326, and 20150299149, or pharmaceutically acceptable salts thereof. The agonists may be agonists of one or both of sphingosine-1-phosphate receptor-1 ($S1P_1$) and sphingosine-1-phosphate receptor-5 ($S1P_5$) and may have little or at least no substantial agonist activity against other sphingosine-1-phosphate receptors (in a mammal such as a human). The sphingosine-1-phosphate receptor agonist used may, for example, be 5-[3-[(1S)-1-(2-hydroxyethylamino)-2,3-dihydro-1H-inden-4-yl]-1,2,4-oxadiazol-5-yl]-2-propan-2-yloxybenzonitrile (also known as ozanimod and RPC1063) or a pharmaceutically acceptable salt thereof such as but not limited to a hydrochloride salt. The structure of ozanimod is shown below.

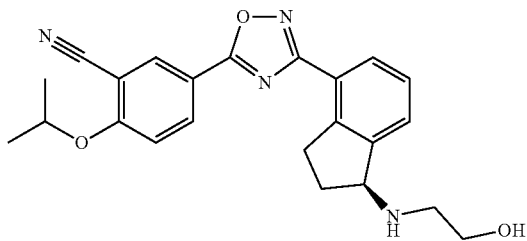 [SMILES: CC(C)Oc1ccc(-c2nc(-c3cccc4c3CC[C@@H]4NCCO)no2)cc1C#N]

See also Scott et al., British Journal of Pharmacology 2016 173:1778-1792.

The sphingosine-1-phosphate receptor agonist may, for example, be etrasimod or a pharmaceutically acceptable salt thereof such as but not limited to a hydrochloride salt. The structure of etrasimod is shown below.

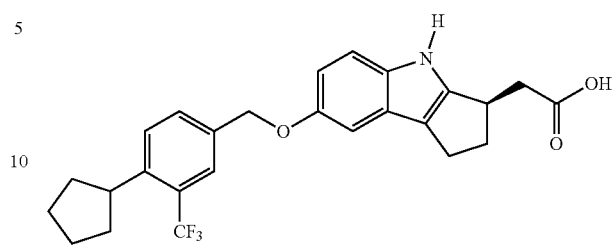

The sphingosine-1-phosphate receptor agonist may, for example, be amiselimod or a pharmaceutically acceptable salt thereof such as but not limited to a hydrochloride salt. The structure of amiselimod is shown below.

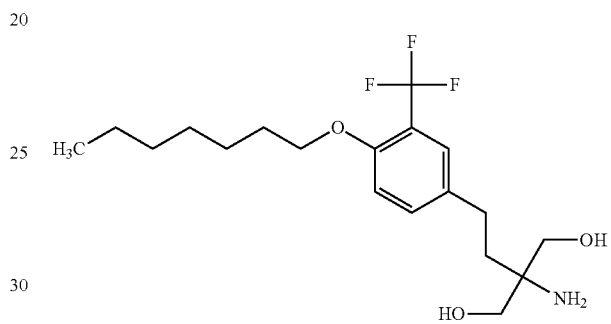

Without limitation, the following embodiments are also provided.

Embodiment 1. A method for treating coronavirus infection in a mammalian subject, such as a human, including the step of:

administering to a mammalian subject in need of treatment for a coronavirus infection an effective amount of a sphingosine kinase type I inhibitor.

Embodiment 2. The method of embodiment 1, wherein the coronavirus infection is severe acute respiratory syndrome coronavirus 2 (SARS-CoV-2) infection.

Embodiment 3. The method of any one of the preceding embodiments, wherein the sphingosine kinase type I inhibitor at least substantially does not inhibit sphingosine kinase type II.

Embodiment 4. The method of any one of the preceding embodiments, wherein the sphingosine kinase type I inhibitor includes a sphingosine kinase type I inhibitor disclosed in U.S. Pat. Nos. 8,372,888 and/or 8,314,151, or a pharmaceutically acceptable salt thereof.

Embodiment 5. The method of any one of embodiments 1-4, wherein the sphingosine kinase type I inhibitor includes SK1-I or a pharmaceutically acceptable salt thereof.

Embodiment 6. The method of any one of the preceding embodiments, wherein said administration includes parenteral administration.

Embodiment 7. The method of embodiment 6, wherein said administration is via injection, such as intravenous injection, intramuscular injection, or subcutaneous injection.

Embodiment 8. The method of any one of embodiments 1-5, wherein said administration includes non-parenteral administration.

Embodiment 9. The method of any one of embodiments 1-5, wherein said administration includes oral administration by ingestion.

Embodiment 10. The method of embodiment 9, wherein said oral administration includes administering a dosage form including the sphingosine kinase type I inhibitor and at least one pharmaceutically acceptable excipient.

Embodiment 11. The method of embodiment 10, wherein the dosage form is selected from the group consisting of a tablet, a capsule, and a gel cap.

Embodiment 12. The method of any one of embodiments 1-5, wherein said administration includes administration via the alimentary canal.

Embodiment 13. The method of any one of the preceding embodiments, further including the step of:
co-administering to the subject an effective amount of ozanimod or a pharmaceutically acceptable salt thereof.

Embodiment 14. A pharmaceutical composition for the treatment of a coronavirus infection in a mammalian subject, such as a human, including:
a therapeutically effective amount of a sphingosine kinase type I inhibitor.

Embodiment 15. The pharmaceutical composition of embodiment 14, wherein the coronavirus infection is severe acute respiratory syndrome coronavirus 2 (SARS-CoV-2) infection.

Embodiment 16. The pharmaceutical composition of any one of embodiments 14 and 15, wherein the sphingosine kinase type I inhibitor at least substantially does not inhibit sphingosine kinase type II.

Embodiment 17. The pharmaceutical composition of any one of embodiments 14-16, wherein the sphingosine kinase type I inhibitor includes a sphingosine kinase type I inhibitor disclosed in U.S. Pat. Nos. 8,372,888 and/or 8,314,151, or a pharmaceutically acceptable salt thereof.

Embodiment 18. The pharmaceutical composition of any one of embodiment 14-17, wherein the sphingosine kinase type I inhibitor includes SK1-I or a pharmaceutically acceptable salt thereof.

Embodiment 19. The pharmaceutical composition of any one of embodiments 14-18, wherein said composition is for parenteral administration.

Embodiment 20. The pharmaceutical composition of embodiment 19, wherein said composition is for administration via injection, such as intravenous injection, intramuscular injection, or subcutaneous injection.

Embodiment 21. The pharmaceutical composition of any one of embodiments 14-18, wherein said composition is for non-parenteral administration.

Embodiment 22. The pharmaceutical composition of any one of embodiments 14-18, wherein said composition is for oral administration by ingestion.

Embodiment 23. The pharmaceutical composition of any one of embodiment 14-22, further including at least one pharmaceutically acceptable excipient.

Embodiment 24. The pharmaceutical composition of any one of embodiments 21 and 22, wherein said composition is a solid dosage form.

Embodiment 25. The pharmaceutical composition of embodiment 24, provided in a dosage form selected from the group consisting of a liquid, a tablet, a capsule, and a gel cap.

Embodiment 26. The pharmaceutical composition of any one of embodiments 14-18, wherein said composition is for administration via the alimentary canal.

Embodiment 27. The pharmaceutical composition of any one of embodiments 14-26, further including a therapeutically effective amount of ozanimod or a pharmaceutically acceptable salt thereof.

Embodiment 28. A method for treating a coronavirus infection in a mammalian subject, such as a human, including the step of:
administering to a mammalian subject in need of treatment for the coronavirus infection, such as a severe acute respiratory syndrome coronavirus 2 (SARS-CoV-2) infection, a therapeutically effective amount of a sphingosine-1-phosphate receptor agonist, such as an agonist of one or both of sphingosine-1-phosphate receptor-1 ($S1P_1$) and sphingosine-1-phosphate receptor-5 ($S1P_5$) such as ozanimod (RPC1063) or a pharmaceutically acceptable salt (such as but not limited to a hydrochloride salt), ester, prodrug, homolog, hydrate or solvate thereof, or an active metabolite of ozanimod or a pharmaceutically acceptable salt (such as but not limited to a hydrochloride salt), ester, prodrug, homolog, hydrate or solvate thereof.

Embodiment 29. The method of embodiment 28, wherein the sphingosine-1-phosphate receptor agonist at least substantially does not agonize sphingosine-1-phosphate receptors other than types-1 and -5.

Embodiment 30. The method of any one of embodiments 28 and 29, wherein the sphingosine-1-phosphate receptor agonist includes a sphingosine-1-phosphate receptor agonist disclosed in any of U.S. Pub. Nos. 20110172202, 20130231326, and 20150299149 or a pharmaceutically acceptable salt (such as but not limited to a hydrochloride salt), ester, prodrug, homolog, hydrate or solvate thereof.

Embodiment 31. The method of any one of embodiments 28-30, wherein the sphingosine-1-phosphate receptor agonist includes ozanimod or a pharmaceutically acceptable salt (such as but not limited to a hydrochloride salt), ester, prodrug, homolog, hydrate or solvate thereof.

Embodiment 32. The method of any one of embodiments 28-31, wherein said administration includes parenteral administration.

Embodiment 33. The method of embodiment 32, wherein said administration is via injection, such as intravenous injection, intramuscular injection, or subcutaneous injection.

Embodiment 34. The method of any one of embodiments 28-31, wherein said administration includes non-parenteral administration.

Embodiment 35. The method of any one of embodiments 34, wherein said administration includes oral administration by ingestion.

Embodiment 36. The method of embodiment 35, wherein said oral administration includes administering a dosage form including the sphingosine-1-phosphate receptor agonist and at least one pharmaceutically acceptable excipient.

Embodiment 37. The method of embodiment 36, wherein the dosage form is selected from the group consisting of a liquid, a tablet, a capsule, and a gel cap.

Embodiment 38. The method of any one of embodiments 28-31, wherein said administration includes administration via the alimentary canal.

Embodiment 39. The method of any one of embodiments 28-38, further including the step of:
co-administering to the subject an effective amount of a sphingosine kinase type I inhibitor, such as SK1-I, or a pharmaceutically acceptable salt thereof.

Embodiment 40. Use of a sphingosine kinase type I inhibitor as disclosed in U.S. Pat. Nos. 8,372,888 and/or 8,314,151, or a pharmaceutically acceptable salt thereof, such as but not limited to a hydrochloride salt, such as SK1-I or a pharmaceutically acceptable salt thereof such as but not limited to a hydrochloride salt, in the treatment of coronavirus infection, such as severe acute respiratory syndrome coronavirus 2 (SARS-CoV-2) infection, in a mammal such as a human patient.

Embodiment 41. Use of a sphingosine-1-phosphate receptor agonist, such as an agonist of one or both of sphingosine-1-phosphate receptor-1 ($S1P_1$) and sphingosine-1-phosphate receptor-5 ($S1P_5$) such as any of those disclosed in U.S. Pub Nos. 20110172202, and 20130231326, and 20150299149, such as ozanimod (RPC1063), or a pharmaceutically acceptable salt (such as but not limited to a hydrochloride salt), ester, prodrug, homolog, hydrate or solvate thereof, or an active metabolite of ozanimod or a pharmaceutically acceptable salt (such as but not limited to a hydrochloride salt), ester, prodrug, homolog, hydrate or solvate thereof, for the treatment of coronavirus infection in mammal, such as the treatment of severe acute respiratory syndrome coronavirus 2 (SARS-CoV-2) infection, in a mammal such as a human patient.

Embodiment 42. Any of the preceding embodiments that involve a sphingosine-1-phosphate receptor agonist, wherein the sphingosine-1-phosphate receptor agonist is a compound having the structure:

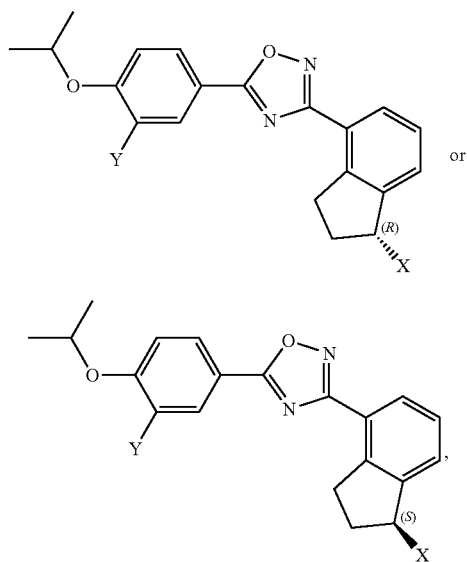

wherein,
X is —NR'R" or —OR'";
Y is —CN, —Cl, or —CF$_3$;
R' is H, C$_{1-4}$ alkyl, n-hydroxy C$_{1-4}$ alkyl, —SO$_2$—R$^1$, or —CO—R$^1$;
R" is H, —SO$_2$—R$^3$, C$_{1-4}$ alkyl optionally substituted with 1 or more R$^2$, or a ring moiety optionally substituted with R$^4$ wherein such ring moiety is piperidinyl, cyclohexyl, morpholinyl, pyrrolidinyl, imidazolyl, or phenyl;
R'" is H, C$_{1-4}$ alkyl, or —CO—R';
or alternatively, R' and R" taken together with the nitrogen atom to which they are bound form a 4-, 5-, or 6-membered saturated heterocyclic ring containing 0 or 1 additional heteroatoms where such additional heteroatom is O or N wherein such heterocycle is optionally singly or multiply substituted with substituents independently selected from —OH, oxo, —NH$_2$, n-hydroxy-C$_{1-4}$ alkyl, —COOH, —(CH$_2$)$_m$—COOH, —(CH$_2$)$_m$—COOR$^1$, —N(R$^1$R$^1$), and —(CH$_2$)$_m$—CO—N(R$^5$R$^5$);
each R$^1$ is independently C$_{1-4}$ alkyl or H;
each R$^2$ is independently H, halo, OH, oxo, =NH, NH$_2$, —COOH, F, —NHR', —N(R$^5$R$^5$), —SO$_2$—R$^1$, —SO$_2$—N(R$^5$R$^5$), —N(R')—SO$_2$—R', —COOR', —OCO—R', —CO—N(R$^5$R$^5$), —N(R')—COR', C$_{1-3}$ alkyl, C$_{1-3}$ alkoxy, and a ring moiety optionally substituted with R$^4$ wherein such ring moiety is piperazinyl, piperidinyl, morpholinyl, pyrrolidinyl, pyrazolyl, imidazolyl, benzimidazolyl, azetidinyl, cyclobutinyl, or phenyl;

each R$^3$ is independently R$^2$, C$_{1-4}$ alkyl, C$_{3-6}$ cycloalkyl, or C$_{1-4}$ alkyl optionally substituted with 1 or more R$^2$;
each R$^4$ is independently halo, OH, —NH$_2$, —NHR$^1$, —N(R'R'), —COOH, —COOR', —NHCO—R$^1$;
each R$^5$ is independently C$_{1-4}$ alkyl or H, or alternatively two R$^5$ taken together with the nitrogen atom to which they are bound can form a 4-, 5-, or 6-membered saturated heterocyclic ring containing 0 or 1 additional heteroatoms where such additional heteroatom is O or N wherein such heterocycle is optionally substituted with —OH, NH$_2$, —N(R'R'), n-hydroxy C$_{1-4}$ alkyl, —(CH$_2$)$_m$—COOH, or —(CH$_2$)$_m$—COOR$^1$; and
each m is independently 0, 1, 2, or 3, or
a pharmaceutically acceptable salt (such as but not limited to a hydrochloride salt), ester, prodrug, homolog, hydrate or solvate thereof.

Embodiment 43. Any of the preceding embodiments that involve a sphingosine-1-phosphate receptor agonist, wherein the sphingosine-1-phosphate receptor agonist is a compound having the structure:

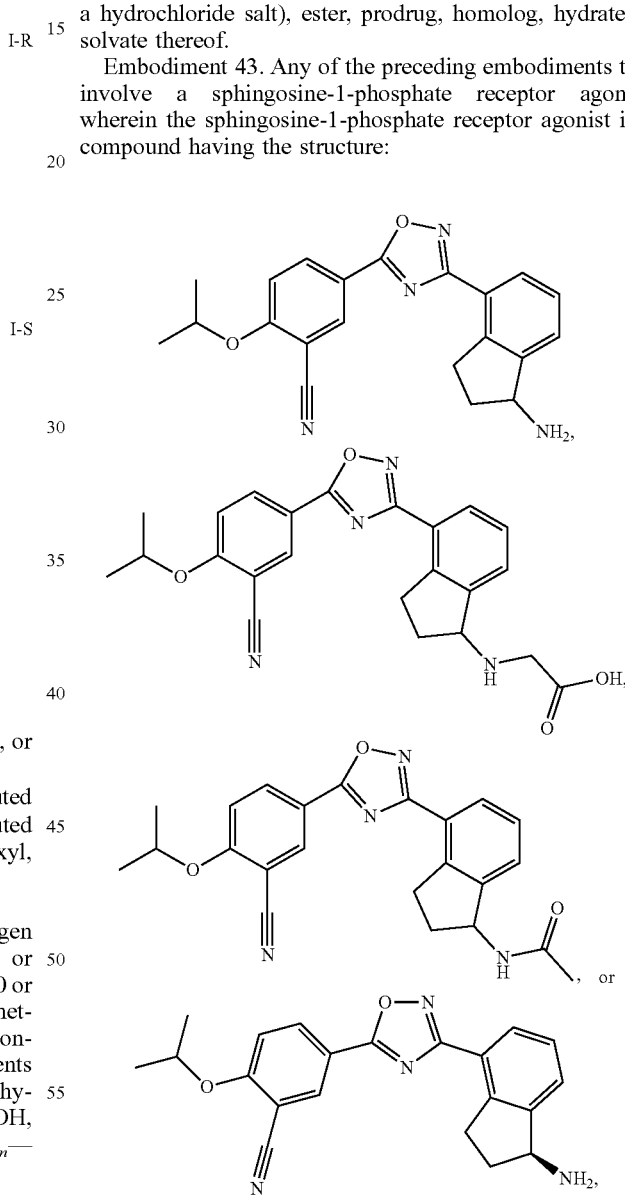

or a pharmaceutically acceptable salt (such as but not limited to a hydrochloride salt), ester, prodrug, homolog, hydrate or solvate thereof. The compounds shown are active metabolites of ozanimod. X may have an (R) or (S) configuration where not specified.

Embodiment 44. Any of the preceding embodiments, wherein the mammal is a human patient in need of treatment for mild Coronavirus disease 2019, medium Coronavirus disease 2019, or severe Coronavirus disease 2019.

It should be understood that wherever this disclosure refers to the treatment of a coronavirus infection generally or particularly, such as treatment of a severe acute respiratory syndrome coronavirus 2 (SARS-CoV-2) infection, treatment of the disease and disease conditions associated with or caused by the coronavirus infection is also being disclosed and is within the scope of treatment of the infection. Accordingly, wherever in this disclosure an embodiment for the treatment of severe acute respiratory syndrome coronavirus 2 (SARS-CoV-2) infection is disclosed, an embodiment for treatment of the corresponding disease, Coronavirus disease 2019 (COVID-19), is also being disclosed.

Administration may be as a single dose or as a divided dose. In one embodiment, an effective dosage is administered once per month until the condition is abated. In another embodiment, the effective dosage is administered once per week, or twice per week or three times per week until the condition is abated. An effective dosage may, for example, be administered at least once daily or at least or at least once every two-days, or at least once every three days, four days, five days, six days or seven days. In another embodiment, an effective dosage amount is administered about every 24 h until the condition is abated. In another embodiment, an effective dosage amount is administered about every 12 h until the condition is abated. In another embodiment, an effective dosage amount is administered about every 8 h until the condition is abated. In another embodiment, an effective dosage amount is administered about every 6 h until the condition is abated. In another embodiment, an effective dosage amount is administered about every 4 h until the condition is abated.

The therapeutically effective doses/amounts of the pharmaceutical compounds disclosed herein may be expressed in terms of the amount of the compound(s) or pharmaceutically acceptable salts thereof administered per unit body weight of the subject per day of treatment, or the total amount administered per day of treatment. A daily dose may, for example, be at least 0.005 mg/kg of body weight, at least 0.01 mg/kg of body weight, at least 0.025 mg/kg of body weight, at least 0.05 mg/kg of body weight, at least 0.1 mg/kg of body weight, at least 0.2 mg/kg of body weight, at least 0.3 mg/kg of body weight, at least 0.4 mg/kg of body weight, at least 0.5 mg/kg of body weight, at least 0.6 mg/kg of body weight, at least 0.7 mg/kg of body weight, at least 0.8 mg/kg of body weight, at least 0.9 mg/kg of body weight, at least 1 mg/kg of body weight, at least 1.5 mg/kg of body weight, at least 2 mg/kg of body weight, at least 2.5 mg/kg of body weight, at least 3 mg/kg of body weight, at least 3.5 mg/kg of body weight, at least 4 mg/kg of body weight, at least 4.5 mg/kg of body weight, at least 5 mg/kg of body weight, or at one of said doses. A total daily dose may, for example, be in the range of 0.005 mg/kg to 5 mg/kg or any subrange or value therein, such as 0.025 to 5 mg/kg body weight, such as 0.05 to 5 mg/kg body weight. A total daily dose may, for example be in the range of 0.1 mg to 1,000 mg total or any subrange or value therein, such as 0.1 mg to 1,000 mg, such as 0.1 mg to 100 mg, such as 0.1 mg to 50 mg, such as 0.5 mg to 50 mg, such as 1.0 mg to 50 mg, such as 5 mg to 50 mg, or 0.1 mg to 10 mg, such as 0.5 mg to 10 mg.

For SK1-I and related SphK1 inhibitors disclosed U.S. Pat. Nos. 8,372,888 and 8,314,151, and pharmaceutically acceptable salts thereof, a total daily dose for human subjects may, for example, also be in the range of 0.5 mg to 100 mg, such as 0.5 mg to 50 mg, such as 0.5 mg to 25 mg, such as 0.5 mg to 20 mg. For SK1-I and related SphK1 inhibitors disclosed U.S. Pat. Nos. 8,372,888 and 8,314,151, and pharmaceutically acceptable salts thereof, a daily dose for human subjects may, for example, also be in the range of 0.5 mg/kg to 5 mg/kg or any subrange or value therein, such as 1 mg/kg to 4 mg/kg, such as 1 mg/kg to 3 mg/kg, or, for example, a total daily dose of 5 mg to 50 mg or any subrange or value therein, such as 10 mg to 40 mg, such as 20 mg to 40 mg.

For ozanimod, its active metabolites and related sphingosine-1-phosphate receptor agonists disclosed in U.S. Pub Nos. 20110172202, 20130231326, and 20150299149, and pharmaceutically acceptable salts thereof, a daily dose for human subjects may, for example, also be in the range of 1 mg to 50 mg or any subrange or value therein, or 0.1 mg to 10 mg or any subrange or value therein, such as 0.1 mg to 5 mg, such as 0.5 to 5 mg, such as 0.5 mg to 2.5 mg, such as 0.5 mg to 1.5 mg. A pharmaceutical composition according to the invention may, for example, include a daily dose amount of the compound as set forth herein.

The duration of treatment by administration of a therapeutic compound or combination according to the invention may continue for a plurality of days, such as for at least one week, at least two weeks, at least three weeks, at least four weeks, at least two months, at least three months, at least four months, at least five months, or generally until symptoms subside.

The terms co-administration and co-administering mean that each of the things being co-administered is administered to a subject in such temporal proximity that each (or its active metabolite(s)) is present in active form in the subject for an at least partially overlapping period of time. Accordingly, co-administration may include, simultaneous administration, such as when the things being administered are part of the same pharmaceutical composition, or sequential administration of the things being co-administered, for example, within the same day of each other, within 12 hours of each other, within 6 hours of each other, within 3 hours of each other, within 1 hours of each other, or within 15 minutes of each other. The things being administered may be administered by the same route, such as by oral ingestion or injection, or by different routes.

Pharmaceutically acceptable salts and the selection and preparation thereof are well known in the art. Such salts include but are not limited to hydrochloride, citrate, glycolate, fumarate, malate, tartrate, mesylate, esylate, cinnamate, isethionate, sulfate, phosphate, diphosphate, nitrate, hydrobromide, hydroiodide, succinate, formate, acetate, dichloroacetate, lactate, p-toluenesulfonate, pamitate, pidolate, pamoate, salicylate, 4-aminosalicylate, benzoate, 4-acetamido benzoate, glutamate, aspartate, glycolate, adipate, alginate, ascorbate, besylate, camphorate, camphorsulfonate, camsylate, caprate, caproate, cyclamate, laurylsulfate, edisylate, gentisate, galactarate, gluceptate, gluconate, glucuronate, oxoglutarate, hippurate, lactobionate, malonate, maleate, mandalate, napsylate, napadisylate, oxalate, oleate, sebacate, stearate, succinate, thiocyanate, undecylenate, and xinafoate.

It should be noted that the indefinite articles "a" and "an" and the definite article "the" are used in the present application to mean one or more unless the context clearly dictates otherwise. Further, the term "or" is used in the present application to mean the disjunctive "or" or the conjunctive "and." It should also be understood that wherever in the present application the term comprising or including (or a term of similar scope) is recited in connection with the description of any embodiment or part thereof, a corresponding embodiment or part thereof reciting instead the term consisting essentially of or the term consisting of (or a term of similar scope) is also disclosed. It should also be understood that wherever a chemical structure or chemical group disclosed herein has one or more stereoisomers or stereoisomeric forms, corresponding embodiments directed to each of the stereoisomers or stereoisomeric forms individually or to any combination of the particular stereoisomers or stereoisomeric forms are also intended to be disclosed.

All publications, patents, patent applications and other documents cited in this application are hereby incorporated by reference in their entireties for all purposes.

While various specific embodiments have been illustrated and described, it will be appreciated that various changes can be made without departing from the spirit and scope of the invention(s). Moreover, features described in connection with one embodiment of the invention may be used in conjunction with other embodiments, even if not explicitly exemplified in combination within.

What is claimed is:

1. A method for treating a severe acute respiratory syndrome coronavirus 2 (SARS-CoV-2) infection in a mammal, comprising the step of:
    administering to a mammal in need of treatment for a severe acute respiratory syndrome coronavirus 2 (SARS-CoV-2) infection a therapeutically effective amount of a compound having the structure

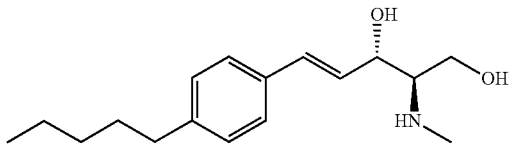 [SMILES: CCCCCc1ccc(/C=C/[C@H](O)[C@@H](CO)NC)cc1]

or a pharmaceutically acceptable salt thereof.

2. The method of claim 1, wherein the mammal is a human patient.

3. The method of claim 1, wherein the administering step comprises administering the hydrochloride salt of the compound to the mammal.

4. The method of claim 3, wherein the mammal is a human patient.

5. The method of claim 2, wherein the human patient has severe Coronavirus disease 2019 (COVID-19).

6. The method of claim 4, wherein the human patient has severe Coronavirus disease 2019 (COVID-19).

* * * * *